US008644608B2

(12) United States Patent
Lavoie et al.

(10) Patent No.: US 8,644,608 B2
(45) Date of Patent: Feb. 4, 2014

(54) BONE IMAGERY SEGMENTATION METHOD AND APPARATUS

(75) Inventors: Frederic Lavoie, Montreal (CA); Said Benameur, Anjou (CA)

(73) Assignee: Eiffel Medtech Inc., Montréal QC (CA)

( * ) Notice: Subject to any disclaimer, the term of this patent is extended or adjusted under 35 U.S.C. 154(b) by 815 days.

(21) Appl. No.: 12/609,839

(22) Filed: Oct. 30, 2009

(65) Prior Publication Data

US 2011/0103654 A1    May 5, 2011

(51) Int. Cl.
  G06K 9/34    (2006.01)
  G06K 9/00    (2006.01)
  G06K 9/36    (2006.01)

(52) U.S. Cl.
  USPC ........... 382/173; 382/131; 382/128; 382/181; 382/276; 382/284

(58) Field of Classification Search
  None
  See application file for complete search history.

(56) References Cited

U.S. PATENT DOCUMENTS

| | | | |
|---|---|---|---|
| 6,091,841 A | 7/2000 | Rogers et al. | |
| 6,137,898 A | 10/2000 | Broussard et al. | |
| 6,704,439 B1 * | 3/2004 | Lee et al. | 382/131 |
| 6,711,282 B1 | 3/2004 | Liu | |
| 6,983,065 B1 | 1/2006 | Akgul | |
| 7,088,850 B2 * | 8/2006 | Wei et al. | 382/128 |
| 7,636,461 B2 * | 12/2009 | Spies et al. | 382/128 |
| 7,664,329 B2 * | 2/2010 | Boregowda et al. | 382/225 |
| 7,881,540 B2 * | 2/2011 | Neemuchwala et al. | 382/225 |
| 8,165,397 B2 * | 4/2012 | Doretto et al. | 382/181 |
| 8,290,223 B2 * | 10/2012 | Suliga et al. | 382/128 |
| 8,335,360 B2 * | 12/2012 | Christiansen et al. | 382/128 |
| 8,428,327 B2 * | 4/2013 | Bjornerud et al. | 382/131 |
| 8,467,606 B2 * | 6/2013 | Barton | 382/173 |

(Continued)

FOREIGN PATENT DOCUMENTS

| | | |
|---|---|---|
| EP | 2052674 | 4/2009 |
| WO | WO 03/098522 | 11/2003 |
| WO | WO 2004/012584 | 2/2004 |
| WO | WO 2009/059815 | 5/2009 |

OTHER PUBLICATIONS

PCT—International Search Report (ISR)—PCT/CA2010/001680—Feb. 9, 2011.

*Primary Examiner* — Michelle Entezari

(74) *Attorney, Agent, or Firm* — Equinox IP; Franz Bonsang

(57) ABSTRACT

There is described an apparatus and method for recovering a contour of a bone from an input image of the bone with its surrounding tissues. The method comprises receiving the input image; applying in parallel at least three image processing functions to the input image to obtain at least three resulting images indicative of respective features of the input image, at least one of the at least three image processing functions pertaining to a spatial domain, and at least another one of the at least three image processing functions pertaining to a frequency domain; combining the at least three resulting images together to form a compounded image, the compounded image identifying at least two regions based on the respective features; identifying the contour of the bone based on the at least two regions of the compounded image; and outputting an output image for display, the output image comprising the contour identified.

19 Claims, 13 Drawing Sheets

(56) References Cited

U.S. PATENT DOCUMENTS

| | | |
|---|---|---|
| 2003/0095698 A1* | 5/2003 | Kawano ................. 382/132 |
| 2004/0008901 A1* | 1/2004 | Avinash ................. 382/260 |
| 2005/0010106 A1 | 1/2005 | Lang et al. |
| 2005/0232474 A1 | 10/2005 | Wei et al. |
| 2006/0170679 A1* | 8/2006 | Wang et al. ............. 345/424 |
| 2007/0110294 A1* | 5/2007 | Schaap et al. ........... 382/131 |
| 2007/0274584 A1* | 11/2007 | Leow et al. ............. 382/132 |
| 2008/0219526 A1* | 9/2008 | Brock-Fisher .......... 382/128 |
| 2009/0129640 A1* | 5/2009 | Stonefield .............. 382/128 |
| 2009/0257637 A1* | 10/2009 | Bohm et al. ............ 382/132 |

\* cited by examiner

BONE IMAGERY SEGMENTATION METHOD AND APPARATUS

CROSS-REFERENCE TO RELATED APPLICATIONS

This is the first application being filed concerning the present description.

TECHNICAL FIELD

This specification relates to the field of medical imagery, and more particularly to image analysis, border detection and segmentation.

BACKGROUND

Prior art image segmentation methods have been applied in medical imaging to detect micro-calcifications in mammogram, to classify cancerous tissues in MRI images, to evaluate bone structures from X-ray images, to detect lesions in images of organs, or to segment and to classify tumors shown in ultrasound images.

It has been found that prior art methods present several shortcomings, such as when segmenting bones represented by ultrasound images. Prior art methods also present issues when attempting to create a bone structure model using various types and qualities of bone images. For example, errors may occur from time to time depending on image quality (e.g. detecting a bone contour where in fact the image shows a tone variation representative of different body tissues). In addition, typical techniques are rather complex and consuming in terms of time and processing resources. Such drawbacks can become quite irritating for a surgeon during a surgical procedure for example.

A need therefore exists to address prior art shortcomings, including complexity and rapidity of execution issues.

SUMMARY

The herein presented apparatus and method for recovering a contour of a bone in an image, thus intends to at least address issues associated with the prior art.

The apparatus and method herein described are applicable in creating electronic bone structure models from images taken on a specific patient. The models thus created are customized to a given patient and provide improved assistance to a surgeon during surgery for example. As such, the herein described apparatus and method are useful in computer-assisted medical applications. For example, images of a patient's member can be automatically processed during a surgical procedure as per the present description, to determine three-dimensional characteristics of a bone. Bone contours and other characteristics thus determined can be displayed to a surgeon in a given spatial coordinate system for example, in order to assist in a medical procedure. The presently described apparatus and method thus alleviate the cumbersome tasks of analyzing multiple images of various types, forms and quality levels, and comparing them to one another before, during and/or after a medical procedure. Better monitoring and diagnosis of a patient's bone condition is also possible from the presently described apparatus and method.

In the present specification, the following terms are meant to be defined as indicated below:

The term "pixel" is intended to refer to a unit picture element which forms part of a digital image. In other words, "pixel" is meant to describe the smallest electronic value used by an electronic apparatus in representing a unit point in an image.

The term "region" is intended to refer to a block of adjacent pixels of substantially similar tone/color values.

The term "contour" is intended to refer to a set of pixels in an image which together form a line separating at least two regions from one another. It should be noted that the prior art often refers to this definition as corresponding to a border.

The term "border" is intended to refer to a set of contours, which once joined in a same coordinate system, define a closed space in two or three-dimensions. It should be noted that the prior art often refers to this definition as corresponding to a contour.

In accordance with an embodiment, the present specification provides an image segmentation method for recovering a contour of a bone from an input image of the bone. The method comprises receiving the input image at a processing device; in the processing device, applying in parallel at least three image processing functions to the input image, to obtain at least three resulting images indicative of respective features of the input image, at least one of the at least three image processing functions pertaining to a spatial domain, and at least another one of the at least three image processing functions pertaining to a frequency domain; in the processing device, combining the at least three resulting images together to form a single compounded image, the compounded image identifying at least two regions based on the respective features, one of the at least two regions corresponding to the bone; in the processing device, identifying the contour of the bone based on the at least two regions of the compounded image; and outputting an output image for display, the output image being based on the compounded image and comprising the contour identified.

In accordance with another embodiment, there is provided an image segmentation apparatus for recovering a contour of a bone from an image of the bone. The apparatus comprises an input device for receiving the image of the bone; an output device for outputting an output image; a processing device; and a memory device in operative communication with the processing device and the input device. The memory device comprises instructions for implementing the processing device to: apply in parallel at least three image processing functions to the image, to obtain at least three resulting images indicative of respective features of the image, at least one of the at least three image processing functions pertaining to a spatial domain, and at least another one of the at least three image processing functions pertaining to a frequency domain; combine the at least three resulting images together to form a single compounded image, the compounded image identifying at least two regions based on the respective features, one of the at least two regions corresponding to the bone; identify the contour of the bone based on the at least two regions of the compounded image; and output the output image to the output device, the output image being based on the compounded image and comprising the contour identified.

In accordance with yet another embodiment, there is provided an image segmentation apparatus for recovering a contour of a bone from an image of the bone. The apparatus comprises at least three image processing units each receiving the image of the bone, the at least three image processing units processing the image to obtain at least three respective results indicative of respective features of the image, at least one of the at least three image processing units processing the image in a spatial domain, and at least another one of the at least three image processing units processing the image in a frequency domain; a combining unit in operative communication with each one of the at least three image processing units for receiving the at least three respective results, and for combining the at least three respective results together to form a compounded result, the compounded result being indicative at least two regions as defined by the respective features, one of the at least two regions corresponding to the bone; and a bone detecting unit in operative communication with the combining unit, for identifying the contour of the bone based on the at least two regions of the compounded result.

DETAILED DESCRIPTION

Figure 1:
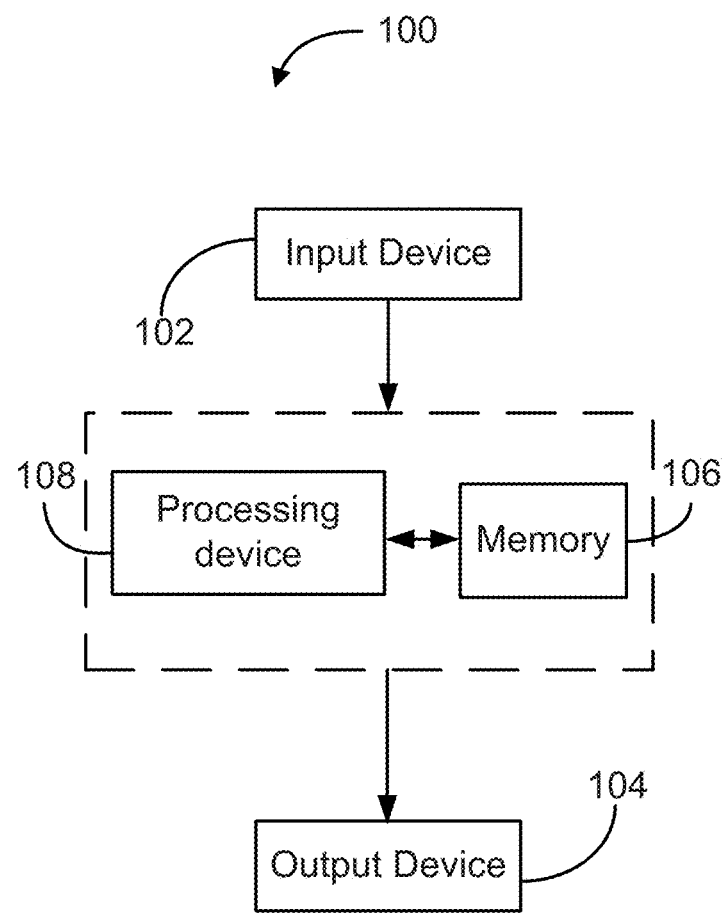
FIG. 1 is a schematic illustration of an apparatus for recovering a contour of a bone from an image of the bone, in accordance with an embodiment.

In reference to FIG. 1, there is illustrated an apparatus 100 for recovering a contour of a bone from an input digital image of the bone. The apparatus 100 has an input device 102, a display device 104, a memory unit 106 and a processing device 108.

The input device 102 receives an input signal representative of an input image of the bone. For example, the input signal has values of entries in an input image matrix representative of the image of the bone. The input image can be any type of image: gray-scale, color, two- or three-dimensional. Various types of medical images are also applicable, such as MRI, X-Ray images, computed tomography (CT), and ultrasound images.

The output device 104 outputs an output image, or an output image matrix representation of the output image, so as to provide the contour of the bone that is recovered by the apparatus 100 from the input image. The output device 104 can be any type of device which uses the recovered bone contour as an input to another image-related process. Alternatively, the output device is simply a display device.

The memory 106 is in operative communication with the processing device 108 and receives the input image from the input device 102. The memory 106 also stores instructions, which once run by the processing device 108, implement the processing device 108 to perform a series of tasks on the input image. The input image(s), output image(s) and processed images obtained from various processing steps are also optionally stored in the memory device 106.

Coded instructions from the memory 106 instruct the processing device 108 to apply at least three image processing functions to the input image in a parallel fashion (e.g. each applied to the same input image). In other words, the functions are applied independently and separately from each other on the original input image. The functions are distinct from each other and permit the finding of different features of the image. Applying these three functions (or more; e.g. F functions, where $F \geq 3$) to the input image results in F results, each representative of a single resulting image (i.e., F resulting images).

The F resulting images are each indicative of at least one feature difference between blocks of pixels, or individual pixels, of the input image. The F functions are chosen such that at least one is applied in the spatial domain and at least another one is applied in the frequency domain. Each one of the F functions permits the identification of a specific, distinct feature of the input image, be it related to texture, tone or visual structure. For example, a first function may be chosen to determine a tone distribution of the image; a second function may be chosen to determine a texture characteristic of the image; while a third function may be chosen determine a visual significance of a feature of the input image. If more than three functions are used, a fourth function may be chosen to determine a spatial or structural feature from the input image. Many other types of functions are optionally added and applied to the input image in a similar, parallel fashion, to distinguish more features of the input image.

In order to apply the above-described functions in parallel, the processing device 108 can be a single processing unit which performs the functions F one after each other in time, but each on the input image; or a single parallel-processing unit which is adapted to perform the functions F concurrently. When a single non-parallel processing unit is used, each result obtained from performing one of the functions F is stored in the memory device 106 prior to continuing with another one of the functions F. The processing device 108 can also be a combination of various types of processing units.

Still in reference to FIG. 1, more coded instructions from the memory 106 instruct the processing device 108 to combine the F results (also referred as F resulting images) together to form a single compounded image. Various image compounding techniques can be used, such as a K-means compounding technique. In such an embodiment, the pixels are redistributed in the k classes according to their characteristics in each one of the resulting images.

The compounded image is indicative of all of the feature information found by applying each one of the functions.

The memory device 106, with its instructions, also implements the processing device 108 to identify the contour of the bone based on the compounded image. For example, a set of larger sized unified regions are located on the compounded image, and gradients associated with regions of the input image corresponding to the set of larger sized unified regions, are obtained in order to identify the contour. The processing device 108 is also optionally instructed to form a line demarcation representative of the contour using a contour recovery process applied to the gradients.

The coded instructions from the memory 106 also instruct the processing device 108 to output the output image to the output device 104. The output image is based on the compounded image and identifies the contour as per the indications provided in the compounded image. The output image has the contour of the bone, or indicates its presence by having at least two regions each with a substantially unified tone, sufficiently different from the other to create a contour demarcation. More than one recovered contour can be in the output image. The output image optionally has a contour formed by all of the recovered contours, and possibly a side of the image, connecting together to form a closed region of a substantially unified tone.

Still in reference to FIG. 1, the memory device 106 can be used to store the input image as well as the compounded image and the output image before it is displayed on the output device 104.

Other instructions can be coded and stored in the memory 106 to implement the processing device 108 to scale the input image from an original size to of a reduced size prior to applying the image processing functions F. Image scaling permit greater rapidity of execution and lower use of available processing power and resources. The scaled-down image (or a matrix representation of a scaled-down image) is optionally stored by the memory device 106.

Similarly, once the compounded image is obtained, the processing device is optionally instructed to scale a number or all of the F resulting images; or alternatively the compounded image, back to the original size of the input image. This way, the output image has the same size as the original input image.

Figure 2:
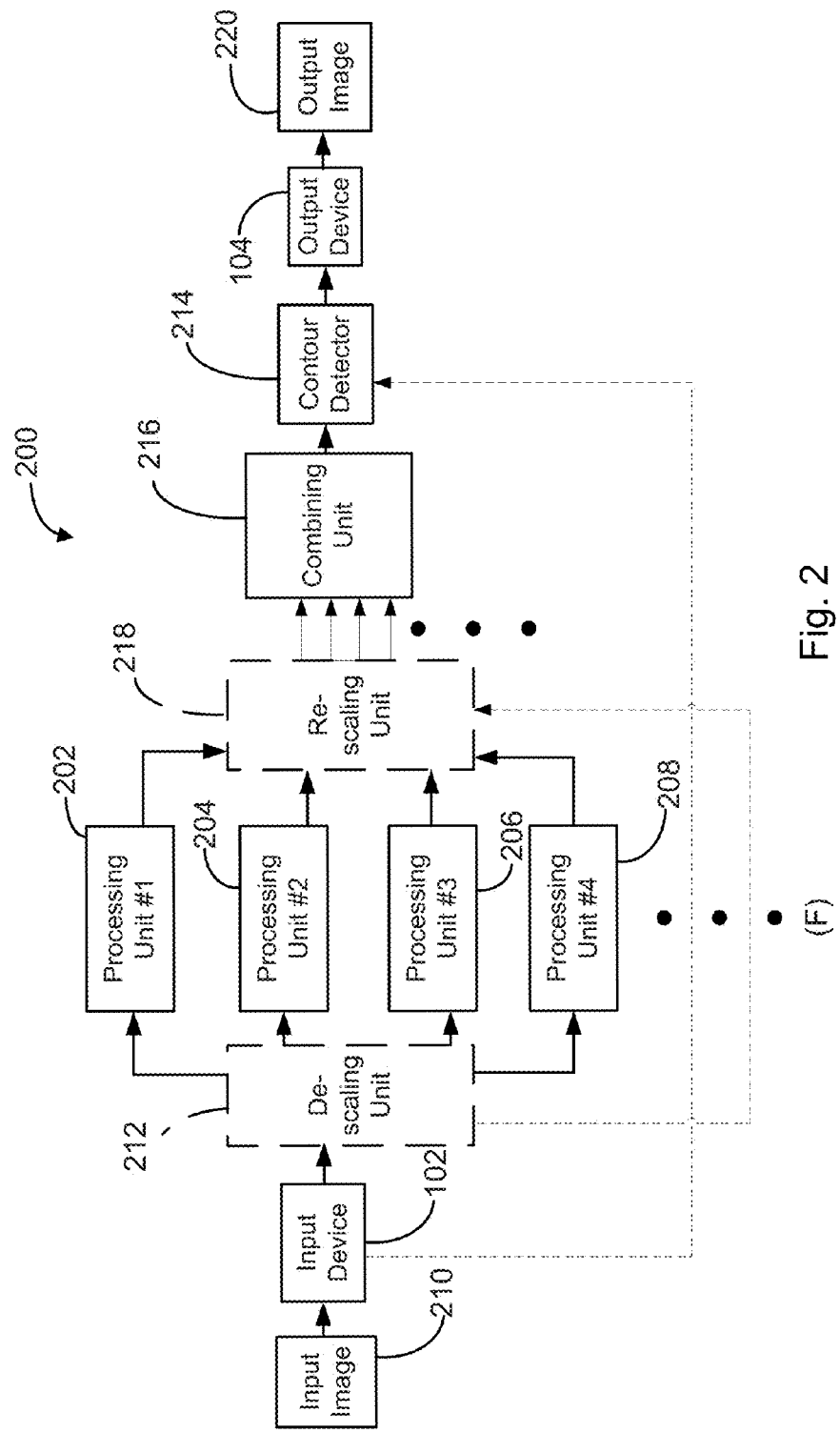
FIG. 2 is a detailed schematic illustration of another apparatus for recovering a contour of a bone from an image of the bone, in accordance with an embodiment.

Now in reference to FIG. 2, there is illustrated an apparatus 200 according to an embodiment in which at least three different image processing units, 202, 204, 206, 208, . . . , (F), are used separately and in parallel to perform different image processing tasks on the input image entered at the input device 102. Again, the input image is an image matrix representation 210 carried over a communication signal for example, or residing in a local or remote memory unit (not shown) or other support medium such as a hard drive, or a removable disk.

The input image 210 is communicated by the input device 102 to each one of the processing units 202, 204, 206, 208, . . . , and (F), via an optional de-scaling unit 212. The input device 102 also communicates the input image 210 to a contour detecting unit 214.

In FIG. 2, each one of the processing units, 202, 204, 206 and 208, . . . , (F) applies a single one of the image processing functions F mentioned above in reference to FIG. 1. Similarly, in FIG. 2, each of the units 202, 204, 206, 208, . . . , (F) outputs a respective result as also mentioned above in relation to FIG. 1.

A combining unit 216 combines together the F results each outputted by respective processing units, 202, 204, 206, 208, . . . (F) to obtain and output a compounded result (or corresponding compounded image) representative of all of the feature differences of each one of the F results obtained from each of the processing units (F). The compounded image has multiple regions, one of which is associated with the bone.

The contour detector 214 receives the compounded result from the combining unit 216 and identifies the contour of the bone therefrom, as per a process described hereinabove in relation to the processing unit 108 of FIG. 1.

Still in reference to FIG. 2, the output device 104 receives the input image 210 from the input device 102, and the identified contour from the contour detector 214.

The output device 104 outputs an output image based on the compounded image and the contour of the bone. The output image is digital and represented by an output image matrix 220.

In FIG. 2, the optional de-scaling unit 212 may scale down the input image to send a scaled-down input image to only one or more of the processing units (any one or more of units 202 to F). In such a case, an optional re-scaling unit 218 re-scales the resulting image(s) outputted by the respective only one or more of the processing units such that all of the re-scaled resulting images sent to the combining unit 216 are of the same size prior to being combined together.

In an alternative to FIG. 2, the re-scaling unit 218 is after the combining unit 216. This case is feasible when all the processing units 202 to F received a scaled-down input image (i.e. the sizes of all of the resulting images are equivalent).

In still another alternative to FIG. 2, the re-scaling unit 218 is in operative communication only with the combining unit 216 and the output device 104, while the contour detector 214 communicates the contour directly to the output device 104.

In still another alternative to FIG. 2, the re-scaling unit 218 is embodied as multiple re-scaling units (or F re-scaling units) each operatively coupled to, or forming part of, each one of the processing units 202, 204, 206, 208, . . . (F). Similarly for the de-scaling unit 212.

The De-scaling and Re-scaling units 212 and 218 are optional and used to reduce the input image in size prior to processing, as well as to increase the output image's size to correspond to the original size of the input image. A scaling factor is communicated between the scaling units 212 and 218. In an embodiment having the scaling unit 212, unit 212 alternatively communicates the scaled-down input image to the contour detector 214.

In FIG. 2, each one of the processing units 202, 204, 206, 208, . . . , (F) are electronic filtering devices which may be implemented as programmable logic devices, for example, programmed to have a specific response equivalent to the function they are each specifically meant to apply to the input image.

It should be noted that both of the apparatuses 100 and 200 of FIGS. 1 and 2 optionally comprise an image acquisition device or a scanning device (not shown) operatively coupled to the input device 102, for either taking an image of a bone or scanning an image of a bone that is not already available in digital format.

Figure 3:
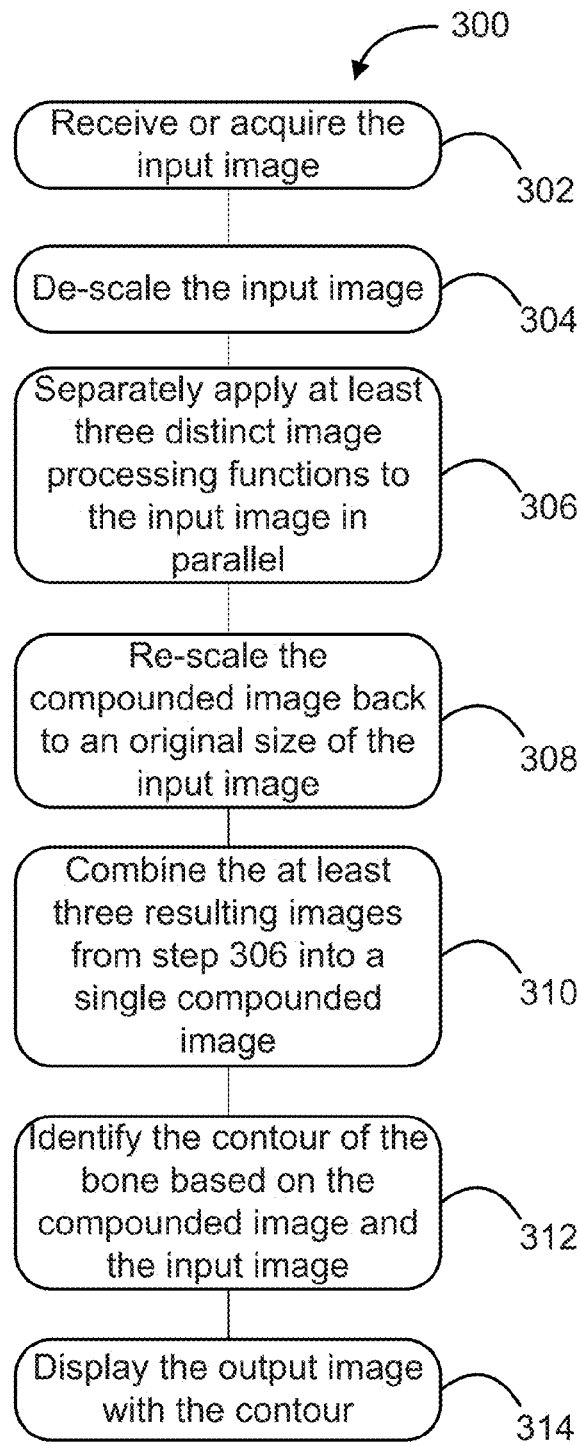
FIG. 3 is a flow chart illustrating a method for recovering a contour of a bone from an image of the bone, in accordance with an embodiment.

Now in reference to FIG. 3, a flow chart illustrates a method 300 for recovering a contour of a bone from an input image of the bone.

In step 302, the input image is received at an input of a processing device. Alternatively, the input image is first acquired by a digital image acquisition device.

Step 304 is optional and involves scaling the input image from an original size of the input image to of a reduced size (e.g. de-scaling), to obtain a scaled-down (or de-scaled) image.

In step 306, a processing device separately applies, in parallel, at least three image processing functions to the input image (or to the scaled-down image), to respectively obtain at least three resulting images. Each one of the resulting images is indicative of respective features (or distinct differences in texture, tone or any other aspect) between blocks of pixels, or individual pixels, of the input image. At least one of the image processing functions pertains to a spatial domain, while at least another one of the image processing functions pertains to a frequency domain.

As in step 304, step 308 is optional and involves scaling the resulting images back to the original size of the input image (e.g. re-scaling). The re-scaling uses a scaling factor which was used in step 304 to de-scale the input image. Various types of multi-scaling techniques are usable to achieve steps 304 and 308. If step 304 is achieved, step 308 is generally performed as well.

In step 310, the at least three resulting images are combined together in the processing device to form one, single compounded image. The compounded image identifies at least two regions in light of the respective features; one of the regions corresponds to the bone.

In step 312, the contour of the bone is identified in the processing device based on the compounded image, or more specifically the regions identified in the compounded image.

In step 314, an output image is outputted from the processing device for display to an output device. The output image is based on the compounded image and comprises the contour identified in step 312. The contour may be displayed as a line demarcation on the compounded image. In an embodiment, the output image represents the bone of the input image segmented therefrom.

In the above-described method, step 308 can also be performed after step 310 if all of the resulting images from step 306 are equivalent in size. This is the case, for example, if a scaled-down version of the input image is provided by step 304 and the image processing functions applied thereto.

Still in reference to FIG. 3, in one embodiment, the above mentioned step 310 optionally involves redistributing the pixels in the k classes according to their characteristics in each one of the resulting images, using a K-means algorithm.

In the above mentioned step 312, a sorting of the various regions detectable from the compounded image is performed according to their respective sizes. Once this is achieved, a number of the regions having the largest sizes are identified and located on the input image. Tone gradients associated with each one of the number of regions having the largest sizes are determined from the input image (or its scaled-down version). The contour is then detected based on these tone gradients. A highest tone gradient is typically associated with the presence of a bone contour since bones are typically lighter in tone than their surroundings. Such tone gradient assumptions can be reversed or adapted for specific input images. Any suitable contour generating process can be used in step 310 to generate an image with a contour demarcation based on the specific tone gradients associated to regions defining the contour. An example of such a contour generating process can be based on any algorithm for tracking a boundary border.

As per the above-described apparatuses, the method 300 is adaptable to recover a contour from any type of digital image, in two or three-dimensions.

In one embodiment, the above-described method 300 is optionally applied to multiple input images which may each represent a bone from varying angles and depths. From these images, a bone contour can be recovered in a three-dimensional coordinate system (x, y and z, where z is a depth axis). In such an embodiment, the multiple two-dimensional input images are processed to find a contour in each one of the images. Once all the contours are recovered for varying depths, they are translated into a same coordinate system, or compared with respect to each other in terms of their (x, y) coordinates and their depth (z). A three-dimensional output image is thus outputted showing a three-dimensional border of the bone. This method is applicable to various medical domains, in which various types of computer models of a patient's anatomy are constructed based on data gathered directly from the patient. This way, personalized computer models of patients' bone structures can be created for use in medical treatment, surgery procedures and other medical interventions.

In addition to creating personalized computer models, three-dimensional contour recovery can be achieved during surgical intervention. An imaging probe is used to acquire images of the bone, while a depth indicator such as a needle is used to gather depth (z) coordinate values associated with each image being acquired.

Still in reference to the method 300 and FIG. 3, the application of the functions to the input image in step 306 optionally involves, for example, passing an image matrix A representative of the input image under analysis, to various distinct image processing devices.

The functions may be chosen in terms of desired feature detection. For example, the functions pertaining to the spatial domain may include functions for calculating a tone distribution histogram of pixels in the input image, texture characterization functions which may or may not be based on statistical methods, and other spatial filters which operate on pixel values as well as their positions. The application of each distinct function generates one or more resulting images which are each indicative of a specific aspect and/or feature of the input image. For example, if tone distribution information of the input image is obtained by applying a quantized histogram function, the resulting image or set of resulting images are formed from the obtained tone distribution information.

A non-exhaustive list of functions applicable to a grayscale input image for example, is provided below with their related mathematical expressions:

Re-Quantized Histogram:

Let $b(x) \in (0, \ldots, N_b-1)$ denote the bin index associated with the gray vector $y(x)$ at pixel location x and $N(x)$ be the set of pixel locations within the squared neighbourhood region centred at pixel location x.

An estimate $h(x)=h(n;x)_{n=0,\ldots,N_{b-1}}$ of bin descriptors characterizing the gray distribution for each pixel to be classified, is given by the following standard bin counting procedure:

$$h(n:x) = k \sum_{u \in N(x)} \partial[b(u) - n] \quad (1)$$

where K is the Kronecker delta function and $$k = \frac{1}{N_\omega^2}$$

is a normalization constant ensuring that:

$$\sum_{R=0}^{N_b-1} h(n:x) = 1 \quad (2)$$

Haralick's Texture Features:

This function concentrates on the spatial statistics involved in associating texture features with tone levels of an image. The below provided example is for a gray scale, two-dimensional image. The method and equation presented herein is however adaptable to color images and three-dimensional images, either in gray scale or color.

One method of identifying texture features in an image is by applying a matrix function to obtain what is best known as the co-occurrence matrix. In 1973, Haralick proposed a set of second-order statistics in order to describe the co-occurrence function p of a gray scale image, also termed the gray-level co-occurrence matrix G. Such a matrix is square with dimension $N_g$, where $N_g$ is the number of gray levels in the image. In other words, the matrix G has a number of rows and columns each equivalent to a number of gray levels in a particular image being analysed.

Briefly summarized, an matrix entry [I, j] of the gray-level co-occurrence matrix G is generated by counting a number of times a pixel with value i is adjacent to a pixel with value j; and then dividing the entire image matrix A representative of the image under analysis, by the total number of such comparisons made. Each entry of the co-occurrence matrix G is therefore considered to represent the probability that a pixel with value i is found adjacent to a pixel of value j in the image analyzed.

Since adjacency of pixels can be defined to occur in each of the four directions in a two-dimensional, square pixel image (horizontal, vertical, left and right diagonals), four of such matrices G are calculated as such:

$$G = \begin{pmatrix} p(1,1)p(1,2) & \cdots & p(1,N_g) \\ \vdots & \ddots & \vdots \\ p(N_g,1)p(N_g,2) & \cdots & p(N_g,N_g) \end{pmatrix} \quad (3)$$

Various texture features can then be determined based on the above co-occurrence matrix G. A non-exhaustive list of such features and associated equations is provided below as examples:

$$\text{Angular Second Moment:} \sum_i \sum_j p(i,j)^2 \quad (4)$$

$$\text{Contrast:} \sum_{n=0}^{N_g-1} n^2 \left( \sum_{i=1}^{N_g} \sum_{j=1}^{N_g} p(i,j) \right), |i-j|=n \quad (5)$$

$$\text{Correlation:} \frac{\sum_i \sum_j (ij)p(i,j) - \mu_x \mu_y}{\sigma_x \sigma_y} \quad (6)$$

where $\mu_x$, $\mu_y$, $\sigma_x$, and $\sigma_y$ are the means and std. deviations of $p_x$ and $p_y$ the partial probability density functions.

$$\text{Sum of Squares - Variance:} \sum_i \sum_j (i-\mu)^2 p(i,j) \quad (7)$$

$$\text{Inverse Difference Moment:} \sum_i \sum_j \frac{1}{1+(i-j)^2} p(i,j) \quad (8)$$

$$\text{Sum Average:} \sum_{i=2}^{2N_g} i p_{x+y}(i) \quad (9)$$

where x and y are the coordinates (row and column) of an entry in the co-occurrence matrix G, and $p_x+p_y(i)$ is the probability of the co-occurrence matrix coordinates summing to x+y.

$$\text{Sum Variance:} \sum_{i=2}^{2N_g} (i-f_s)^2 p_{x+y}(i) \quad (10)$$

$$\text{Sum Entropy:} -\sum_{i=2}^{2N_g} p_{x+y}(i)\log(p_{x+y}(i)) = f_s \quad (11)$$

$$\text{Entropy:} -\sum_i \sum_j p(i,j)\log(p(i,j)) \quad (12)$$

$$\text{Difference Variance:} \sum_{i=0}^{N_g-1} i^2 p_{x-y}(i) \quad (13)$$

$$\text{Difference Entropy:} -\sum_{i=0}^{N_g-1} p_{x-y}(i)\log(p_{x-y}(i)) \quad (14)$$

$$\text{Information Measure of Correlation 1:} \frac{HXY - HXY1}{\max(HX, HY)} \quad (15)$$

Information Measure of Correlation 2: (16)

$$(1 - \exp(-2(HXY2 - HXY)))^{\frac{1}{2}}$$

where $HXY = \sum_i \sum_j p(i,j)\log(p(i,j))$, $HX$, $HY$ are the entropies of $p_x$ and $p_y$;

where $HXY1 = -\sum_i \sum_j p(i,j)\log(p_x(i)p_y(j))$; ; and where $HXY2 = -\sum_i \sum_j p_x(i)p_y(j)\log(p_x(i)p_y(j))$;

Maximum Correlation Coefficient: represented by the square root of the second largest eigenvalue of Q, where:

$$Q(i,j) = \sum_k \frac{p(i,k)p(j,k)}{p_x(i)p_y(k)} \quad (17)$$

The Discrete Cosine Transform (DCT):

The discrete cosine transform (DCT) is applied to represent the image under analysis as a sum of sinusoids of varying magnitudes and frequencies. Once the DCT of an image is obtained, visually significant information about the image is distinguishable from its concentration in a few coefficients of the DCT. A mathematical representation of the DCT is as follows:

$$X_{k1,k2} = \sum_{n_1=0}^{N_1-1} \sum_{n_2=0}^{N_2-1} x_{n1,n2} \cos\left(\frac{\pi}{N_1}\left(n_1+\frac{1}{2}\right)k_1\right)\cos\left(\frac{\pi}{N_2}\left(n_2+\frac{1}{2}\right)k_2\right) \quad (18)$$

The Gabor Filter:

The Gabor filter is a function in the spatial domain which is best described as a Gaussian function modulated by a sinusoidal curve; and may be mathematically represented as:

$$g(x,y) = \exp(2j\pi(\mu_o x + \vartheta_o y))\exp\left(-\left(\frac{(x-x_o)^2}{\sigma_x} + \frac{(y-y_o)^2}{\sigma_y}\right)\right) \quad (19)$$

As mentioned hereinabove, these segmentation functions are examples and others which are not mentioned above can be used.

Now in reference to FIGS. 4 to 13, there are illustrated various images from various stages of the method 300 of FIG. 3.

Figure 4:
FIG. 4 is an example of a gray-scale ultrasound input image of a bone input in accordance with an embodiment.

FIG. 4 is an example of a gray-scale ultrasound input image of a bone and surrounding tissue that could be received at step 302 of FIG. 3.

Figure 5:
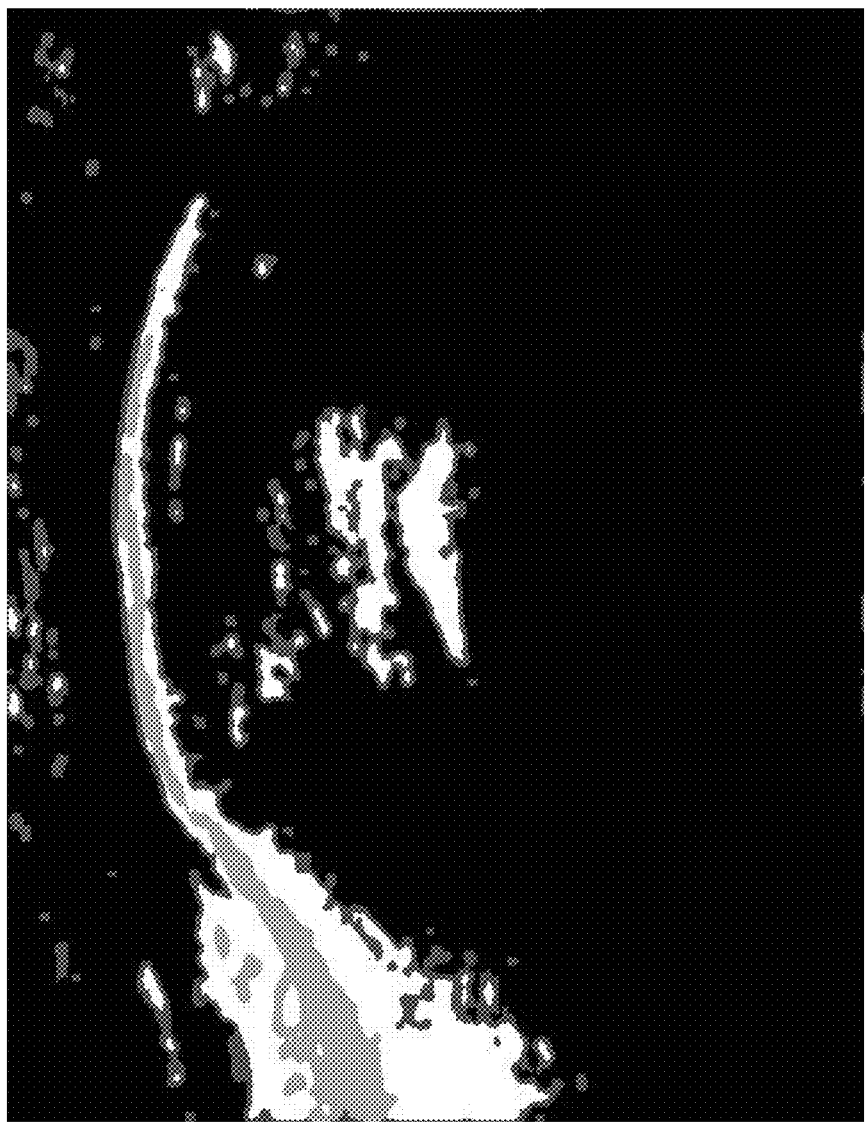
FIG. 5 is an example of a processed image resulting from the application of a first function on the input image of FIG. 4, in accordance with an embodiment.
Figure 6:
FIG. 6 is an example of a processed image resulting from the application of a second function on the input image of FIG. 4, in accordance with an embodiment.
Figure 7:
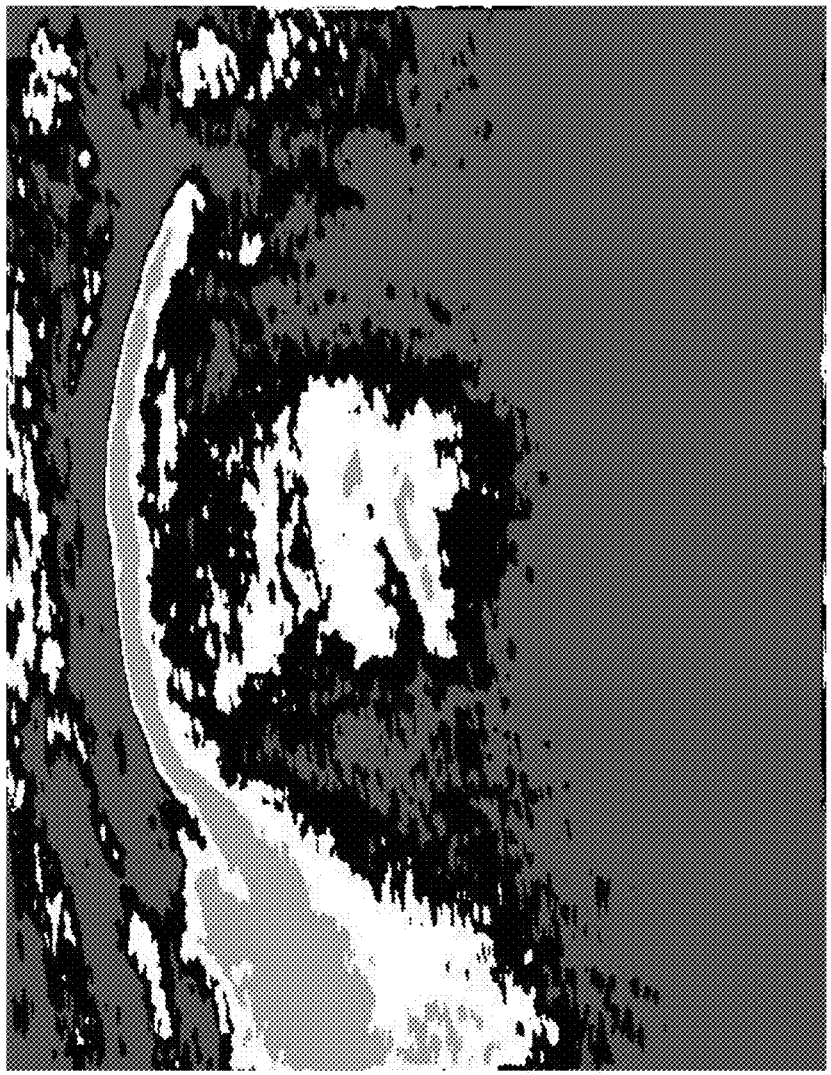
FIG. 7 is an example of a processed image resulting from the application of a third function on the input image of FIG. 4, in accordance with an embodiment.
Figure 8:
FIG. 8 is an example of a processed image resulting from the application of a fourth function on the input image of FIG. 4, in accordance with an embodiment.

FIG. 5 through 8 each show different resulting images obtained after respectively applying four functions as per step 306 of FIG. 3. FIG. 5 is an example of first processed image resulting from the application of a function comprising a quantified histogram function; FIG. 6 is an example of second processed image resulting from the application of a function comprising a co-occurrence matrix; FIG. 7 is an example of third processed image resulting from the application of a function comprising a discrete cosine transform (DCT); and FIG. 8 is an example of a fourth processed image resulting from the application of a function comprising a Gabor filter.

Figure 9:
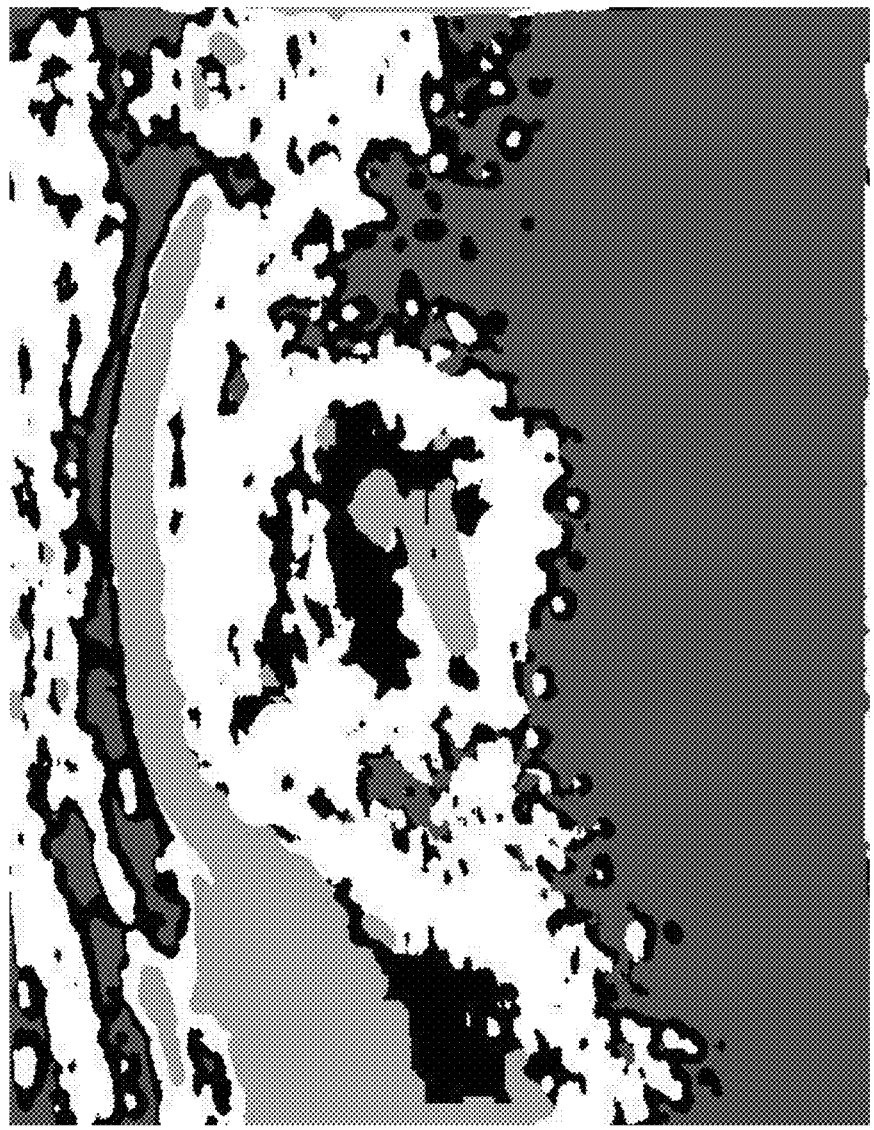
FIG. 9 is an example of a compounded image resulting from the fusion of the processed images of FIGS. 5 to 8, in accordance with an embodiment.

FIG. 9 shows a compounded image formed by fusing the resulting images of FIGS. 5 through 8, as per step 310 of FIG. 3. FIG. 9 has various regions.

Figure 10:
FIG. 10 is the compounded image of FIG. 9, after a first stage leading to the detection of a contour therefrom, in accordance with an embodiment
Figure 11:
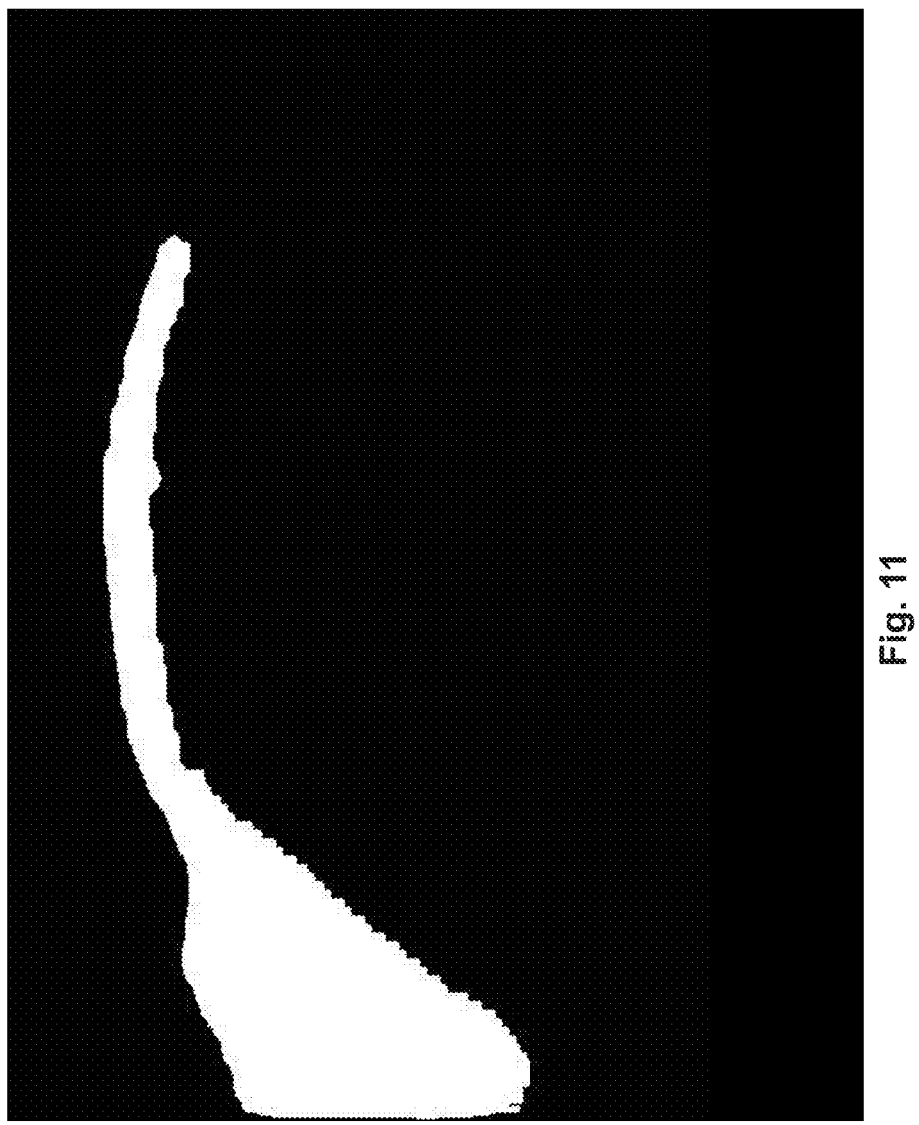
FIG. 11 is the compounded image of FIG. 10, after a next stage leading to the detection of a contour therefrom, in accordance with an embodiment.

FIG. 10 and FIG. 11 each show the compounded image of FIG. 9 at various stages during the contour identification process as per step 312 of FIG. 3. More particularly, FIG. 10 is the compounded image of FIG. 9 after detection of regions likely to contain the body to be detected; while FIG. 11 is the compounded image of FIG. 10 after detection of the regions containing the body to be detected.

Figure 12:
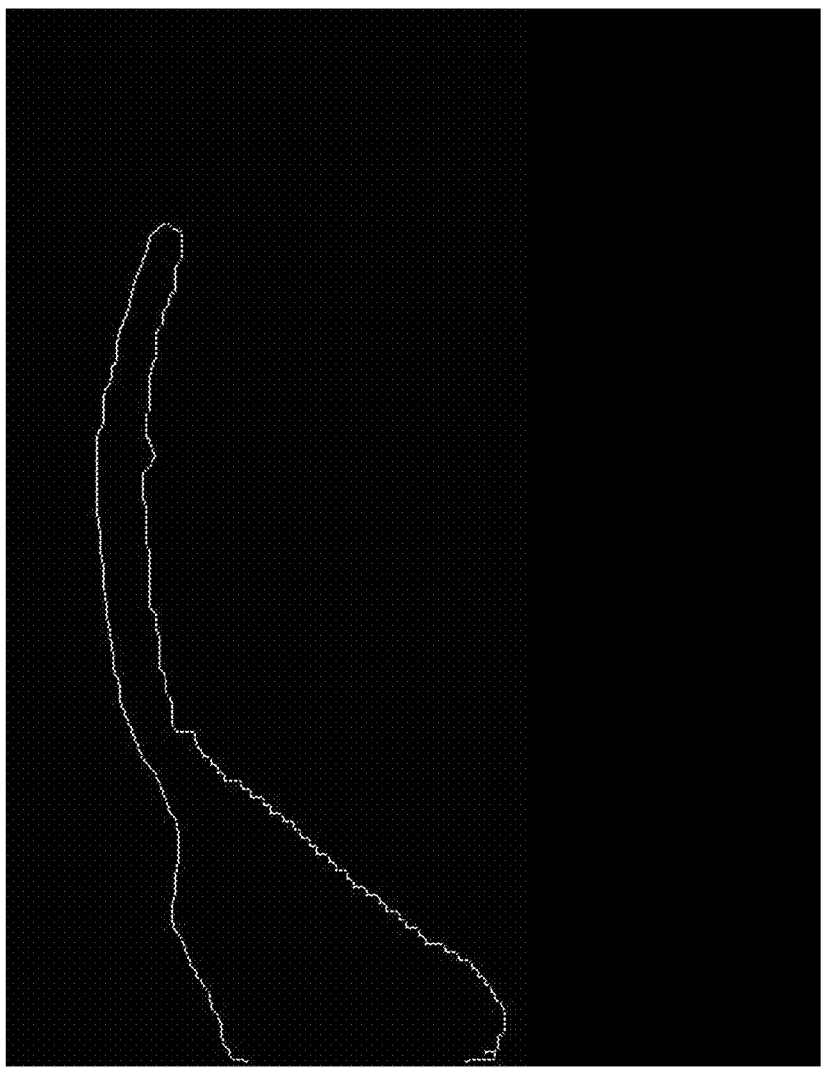
FIG. 12 is an example of an output image with a border, in accordance with an embodiment.
Figure 13:
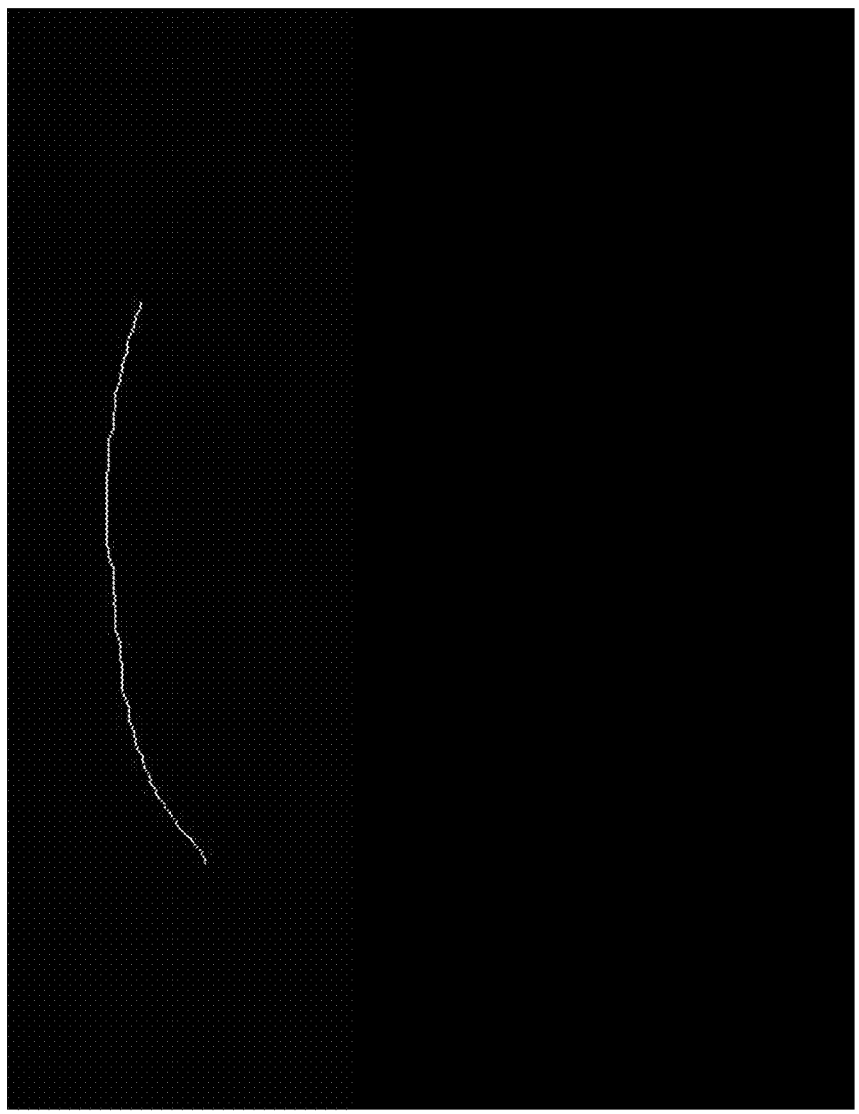
FIG. 13 is an example of an output image with a contour, in accordance with an embodiment.

FIG. 12 and FIG. 13 are examples of output images obtained based on the compounded image of FIG. 11, as per step 314 of FIG. 3. FIG. 12 shows an external border of the region containing the detected body; while FIG. 13 is an example of a contour, here an upper outer edge of the region containing the detected body. FIG. 13 may be obtained from FIG. 12, or may be obtained prior to obtaining the entire external border of FIG. 12 (i.e. at a stage towards completing the border from a plurality of outer edges each forming contours).

While preferred embodiments have been described above and illustrated in the accompanying drawings, it will be evident to those skilled in the art that modifications may be made therein without departing from the intended scope of this specification. Such modifications are therefore considered as possible variants forming part of this specification.

The invention claimed is:

1. An image segmentation method for recovering a contour of a bone from an input image of the bone, the method comprising:
receiving the input image at a processing device;
in the processing device, independently applying at least three distinct image processing functions to the input image, to obtain at least three resulting images indicative of respective distinct features of the input image, at least one of the at least three image processing functions pertaining to a spatial domain, and at least another one of the at least three image processing functions pertaining to a frequency domain;
in the processing device, combining the at least three resulting images together by distributing pixels according to their k-class based on corresponding pixel characteristics in each one of the at least three resulting images to form a single compounded image representative of all of the respective distinct features differences, the compounded image identifying at least two regions based on the respective distinct features, one of the at least two regions corresponding to the bone;
in the processing device, identifying the contour of the bone based on the at least two regions of the compounded image; and
outputting an output image for display, the output image being based on the compounded image and comprising the contour.

2. The method of claim 1, wherein the identifying comprises sorting the at least two regions of the compounded image according to respective sizes; and locating a number of regions associated with larger one of the respective sizes.

3. The method of claim 2, wherein the identifying comprises generating the contour based on tone gradients associated with the number of regions, the tone gradients being obtained from the input image.

4. The method of claim 1, comprising:
scaling the input image from an original size of the input image to a reduced size, to obtain a scaled-down image; wherein the applying at least three image processing functions to the input image comprises applying at least one of the at least three image processing functions to the scaled-down image.

5. The method of claim 4, comprising:
scaling one of: the compounded image and at least one of the at least three resulting images back to the original size of the input image, to obtain the output image.

6. The method of claim 4, wherein the receiving comprises receiving multiple input images of the bone in an (x, y) plane, each one of the multiple input images being acquired at a depth coordinate (z), the method comprising performing the applying, the combining and the identifying for each one of the multiple input images to recover corresponding contours, and translating the corresponding contours in a same three-dimensional coordinate system to generate a border of the bone in three-dimensions.

7. The method of claim 1, wherein the receiving comprise receiving at least one of an ultrasound input image, an MRI image, an X-ray image, a CT image.

8. The method of claim 1, wherein the applying at least three image processing functions comprises:
applying a first function to the input image to obtain a first resulting image based on a tone distribution of the input image;
applying a second function to the input image to obtain a second resulting image based on a texture of the input image; and
applying a third function to the input image to obtain a third resulting image based on a visual significance of a feature of the input image;
wherein the first, second and third resulting images are independent of each other.

9. The method of claim 8, wherein the applying at least three image processing functions further comprises applying a fourth function to the input image to obtain a fourth resulting image based on one of a spatial and structural significance of a given feature of the input image.

10. The method of claim 1, wherein the at least three image processing functions comprise at least one of: a quantized histogram, a gray scale co-occurrence matrix based statistical features function, a discrete cosine transform, and a Gabor filtering function.

11. An image segmentation apparatus for recovering a contour of a bone from an image of the bone, the image segmentation apparatus comprising:
an input device for receiving the image of the bone;
an output device for outputting an output image;
a processing device; and a memory device in operative communication with the processing device and the input device, the memory device comprising instructions for implementing the processing device to:

independently apply at least three distinct image processing functions to the image, to obtain at least three resulting images indicative of respective distinct features of the image, at least one of the at least three image processing functions pertaining to a spatial domain, and at least another one of the at least three image processing functions pertaining to a frequency domain;

combine the at least three resulting images together by distributing pixels according to their k-class based on corresponding pixel characteristics in each one of the at least three resulting images to form a single compounded image representative of all of the respective distinct features differences, the compounded image identifying at least two regions based on the respective distinct features, one of the at least two regions corresponding to the bone;

identify the contour of the bone based on the at least two regions of the compounded image; and output the output image to the output device, the output image being based on the compounded image and comprising the contour identified.

12. The apparatus of claim 11, wherein the memory device comprises instructions for implementing the processing device to:

identify a number of regions associated with larger sizes from the at least two regions of the compounded image; and generating the contour based on tone gradients associated with the number of regions, the tone gradients being obtained from the image.

13. The apparatus of claim 11, wherein the memory device comprises instructions for implementing the processing device to:

scale the image from an original size of the image to of a reduced size, to obtain a scaled-down image, the memory device storing the scaled-down image; and scale one of: the compounded image and at least one of the at least three resulting images back to the original size of the image, to obtain the output image.

14. The apparatus of claim 11, wherein the input device comprises a surgical probe having an image acquisition device.

15. The apparatus of claim 11, wherein the image comprises at least one of an ultrasound input image, an MRI image, an X-ray image, a CT image.

16. The apparatus of claim 11, wherein the memory device comprises instructions for implementing the processing device to:

apply a first function to the image to obtain a first resulting image based on a tone distribution of the image;

apply a second function to the image to obtain a second resulting image based on a texture of the image; and apply a third function to the image to obtain a third resulting image based on a visual significance of a feature of the image; and apply a fourth function to the image to obtain a fourth resulting image based on one of a spatial and structural significance of a given feature of the image;

wherein the first, second, third and fourth resulting images are independent of each other.

17. An image segmentation apparatus for recovering a contour of a bone from an image of the bone, the image segmentation apparatus comprising:

at least three image processing units each receiving the image of the bone, the at least three image processing units independently and distinctly processing the image to obtain at least three respective results indicative of respective distinct features of the image, at least one of the at least three image processing units processing the image in a spatial domain, and at least another one of the at least three image processing units processing the image in a frequency domain;

a combining unit in operative communication with each one of the at least three image processing units for receiving the at least three respective results, and for combining the at least three respective results together by distributing pixels according to their k-class based on corresponding pixel characteristics in each one of the at least three resulting images to form a compounded result representative of all of the respective distinct features differences, the compounded result being indicative at least two regions as defined by the respective distinct features, one of the at least two regions corresponding to the bone; and a bone detecting unit in operative communication with the combining unit, for identifying the contour of the bone based on the at least two regions of the compounded result.

18. The image segmentation apparatus of claim 17, comprising a scaling unit operatively coupled to at least one of: the combining unit, and at least one of the at least three image processing units, for de-scaling and re-scaling an image size.

19. The image segmentation apparatus of claim 17, comprising an output device in operative communication with the combining unit, for outputting an output image based on the compounded result and the contour.

* * * * *